United States Patent [19]

Sava

[11] Patent Number: 5,658,286
[45] Date of Patent: Aug. 19, 1997

[54] FABRICATION OF IMPLANTABLE BONE FIXATION ELEMENTS

[76] Inventor: Garard A. Sava, 80 Mill River St., Stamford, Conn. 06902

[21] Appl. No.: 596,676

[22] Filed: Feb. 5, 1996

[51] Int. Cl.[6] .............................. A61B 17/58; A61B 19/00
[52] U.S. Cl. ........................... 606/61; 606/60; 264/4
[58] Field of Search ...................... 606/61, 60; 623/901; 425/2; 264/4

[56] References Cited

U.S. PATENT DOCUMENTS

| | | | |
|---|---|---|---|
| 3,707,146 | 12/1972 | Cook et al. | 128/780 |
| 4,653,481 | 3/1987 | Howland et al. | |
| 4,773,402 | 9/1988 | Asher et al. | |
| 5,030,220 | 7/1991 | Howland | |
| 5,290,289 | 3/1994 | Sanders et al. | |
| 5,303,718 | 4/1994 | Krajicek | 128/897 |
| 5,373,860 | 12/1994 | Catone | |
| 5,397,361 | 3/1995 | Clark | |

FOREIGN PATENT DOCUMENTS

| | | | |
|---|---|---|---|
| 1745231 | 5/1990 | U.S.S.R. | |
| 9421185 | 9/1994 | WIPO | 606/61 |

OTHER PUBLICATIONS

Dickson, R.A., and Bradford, D.S., eds., *Management of Spinal Deformities*, Butterworths, London, 1984. pp. 194-204.

*Primary Examiner*—Guy V. Tucker
*Assistant Examiner*—Julian W. Woo
*Attorney, Agent, or Firm*—St. Onge Steward Johnston & Reens

[57] ABSTRACT

A method for shaping an implantable rigid bone fixation element during surgery involves inserting into at least two bones or bone parts a securing means for the element, with each means engageable with and defining a shape for the element; seating a flexible housing such as tubing having a contour essentially the same as the element into the engaging means; injecting a quick-setting fluid molding material into the housing; curing the molding material for a time under conditions sufficient to harden the material so that the housing forms a temporary master; and removing the temporary master and using it as a template to form the element. The method is especially preferred for the fabrication of spinal support bars, and provides for rapid and precise bar shaping.

15 Claims, 3 Drawing Sheets

FABRICATION OF IMPLANTABLE BONE FIXATION ELEMENTS

TECHNICAL FIELD

This invention relates to a method for shaping implantable rigid bone fixation elements, particularly spinal column support bars.

BACKGROUND OF THE INVENTION

Metal plates, screws, wires, and bars have been used since the nineteenth century to immobilize bone fragments and correct various types of bone disorders, but only in recent times has the practice become widespread without the serious risks of infection, tissue rejection, and technical failures observed in early procedures. Today utilization of metal support elements are used routinely for the surgical treatment of bone fractures, corrections, and reconstructions.

Although filled, reinforced hosing (Soviet Union Pat. No. 1745231) and rigid polymers have been suggested as alternatives, metal rods or bars are particularly useful for the surgical correction of spinal column disorders such as scoliosis, kyphosis, spondyloisthesis, and remediation of other problems such as ruptured or slipped discs, broken or fractured spinal columns and the like. Stainless steel is often employed (see, for example, U.S. Pat. No. 4,773,402 to Asher and Strippgen, column 3, lines 51 to 53); it is typically chemically polished and passivated so that it resists corrosion by body fluids. A number of systems have been described, variously utilizing hooks, wires, plates, rods, and combinations of these elements with each other and with pins, screws, and other securing means (see, for example, Dickson, R. A., and Bradford, D. S., eds., *Management of Spinal Deformities*, Butterworths, London, 1984, pages 194 to 204). Several methods for contouring these elements have been suggested.

In U.S. Pat. No. 4,653,481, Howland and Wiltse disclosed a spine fixation system with a plurality of screw clamp assemblies that included removable saddle assemblies having apertures proportioned for the reception of rigid support rods. In the installation of the system, screw members were positioned in the spine, and a soft rod, e.g., one made of a soft aluminum alloy, was installed through the apertures, forming a temporary master that could be used to replicate the relative position of the apertures (column 10, line 63 to 66). The soft rod was removed and used as a master for shaping the rigid rods (column 11, lines 61 to 68). In a later patent, Howland employed soft aluminum as a master for a steel rod in a functionally similar spine fixation system that had an improved saddle assembly and a wire protector (U.S. Pat. No. 5,030,220, column 5, lines 39 to 48).

Instead of an aluminum master, Catone described earlier uses of a soft tin alloy for contouring a template in U.S. Pat. No. 5,373,860 (column 2, lines 48 to 50). The patent was directed primarily to bone plate fabrication, particularly for repair of facial bone fractures, and suggested replacing the tin template with a molded impression of the surface area to be repaired; the impression was made by compressing a molding material to the fixation area prior to fabricating an element (column 3, lines 24 to 34). A suggested material was Cranioplast,® generally used by neurosurgeons to recontour bony defects, and, since the monomer employed in its fabrication is described as toxic to the cardiovascular system and locally irritating to tissues, a film was used as a protective interface during formation of the master (column 4, lines 48 to 59). After the molding material had set, a bone plate or other element was made in two steps by applying force to a compression member to obtain an opposing (positive) impression and using this second contoured impression as a template for the element (column 5, lines 16 to 30). Though tedious, the method was described as having advantages over earlier described bone plate fabrications because manual manipulation during surgery was decreased with more precise contouring (column 2, lines 56 to 65). In U.S. Pat. No. 5,397,361, Clark also made an impression and then used Cranioplast® material for fabrication of skull plates, but the procedure was not carried out during surgery; instead, the plate was removed and duplicated (column 3, lines 4 to 5 and 19 to 25).

Sanders, et al., disclosed use of a "shape-memory alloy" such as ninitol (a mixture of nickel and titanium) for fabrication of rods for the surgical correction of scoliosis in U.S. Pat. No. 5,290,289 (column 5, lines 5 to 8). Rod shape was changed with heat; rods made from nitinol, for example, reverted to their original shape when heated above their shape transition temperature (id., lines 9 to 12). Entire rods or localized rod portions could be heated with, for example, a radio frequency induction heater, in order to produce selective correctional forces (column 7, lines 43 to 57). Use of templates was not discussed, but the method required rods be deformed in a certain crystalline state to a shape desired for spine correction before use (column 5, lines 51 to 54). Thus, the method involved a number of steps prior to alteration of the rod shape after installation.

Whatever the method of implant element fabrication, a major element of imprecision remains for surgeons repairing or correcting skeletal structures. The placement and arrangement of securing means and engagement of the means with the element are as critical to a successful outcome to the procedure as the contour of the element, and element alignment, positioning and securing are done manually in the operating room. This is particularly true of spinal column corrections and repairs, where various torsional forces in the vertebrae, in the spine fixation system, and between different vertebrae and the system come into play around delicate spinal nerve tissue. Meticulous care must be taken in the positioning of the securing means and shaping of the support members. If the fixation system is not properly fabricated and installed, wire and rod support members can twist and snap and screws or other securing means can fatigue, break or pull out, often resulting not only in a failure of the operation but also in serious medical complications such as spinal cord trauma for the patient.

Successful implantation of spinal support systems is technically complex and difficult, requiring patience and exceptional manual dexterity as well as surgical skill and experience. The procedure is so fraught with possibilities for complications that it is typically employed only when the prognosis without this type of surgical intervention is poor, or casts, braces, traction, and other nonsurgical support and/or corrective treatments have failed.

Moreover, certain spinal support systems are inherently more complicated to install than others. In postero-lateral fusions with pedicle fixation, for example, proper bending and shaping of the connecting rod is a major obstacle to the success of the procedure. The rod is almost always a compound curve which must connect the screws rigidly without placing asymmetrical torque on the screw or the pedicle involved in the fusion. A trial and error method with a variety of instruments has to date been the only available method of shaping the connecting rod.

It would be desirable to have an alternative method for shaping bone support elements that could be used for rapid fabrication in the operating room under sterile conditions. It would be especially desirable to have such a method for shaping spinal support rods and bars that are precisely contoured, including bars that have compound curves.

SUMMARY OF THE INVENTION

It is an object of the invention to provide a rapid method for fabricating an implantable bone fixation element during surgery.

It is a further and more specific object of the invention to provide a rapid method for fabricating spinal column support bars contoured for a precise fit.

These and other objects are achieved by the present invention, which in most embodiments employs a tubing filled with quick-setting molding material as a guide or template for shaping a bone fixation element after the material has hardened. Briefly stated, the invention provides a method for shaping an implantable rigid bone fixation element during surgery that comprises the steps of inserting into at least two bone parts at least one securing means for the element, each means engageable with the bone and the element and defining a shape for the element after installation in the bone or bones; aligning the bone or bones to be fixed in the desired configuration; seating a flexible housing having an exterior contour essentially the same as the element into the engaging means such that the housing follows the shape of the element; injecting fluid molding material into the housing; curing the molding material for a time under conditions sufficient to harden the material so that the housing forms a temporary master having a shape which replicates the shape of the element; and removing the temporary master and using it as a template to form the element.

In a preferred embodiment, the invention provides a method for shaping an implantable rigid spinal column support bar, including bars having at least one compound curve. The method involves first inserting securing means such as screw clamps or screws in the vertebrae in the portion of the spinal column to be supported by the bar; the securing means have members such as screw clamp members or screw heads that engage and secure the bar. After aligning the column in the desired position, a flexible hollow tubing is seated in the screw clamp members or heads to simulate the final position of the bar, wherein the tubing has an diameter essentially the same as the bar. A quick-setting fluid molding material such as a hydrophilic vinyl polysiloxane marketed as the Reprosil® cartridge system or Dentsply® is injected into the tubing, and allowed to set; in typical embodiments, this takes from about 2.5 to about 10 minutes at room temperature, but the time can be extended if required. The tubing containing the cured molding material is then removed and used as a template for the formation of the bar. In preferred embodiments, two bars are shaped for bilateral support of the spinal column.

Other objects, aspects and features of the present invention in addition to those mentioned above will be pointed out in or will be understood from the following detailed description provided in conjunction with the accompanying drawings.

BRIEF DESCRIPTION OF THE FIGURES

FIG. 2C shows that in a matter of minutes after the material as cured and hardened, the tubing conforms to the proper configuration defined by the geometry of the heads and can be removed for use as a template in fashioning the metal bar.

DETAILED DESCRIPTION OF THE INVENTION

Figure 1:
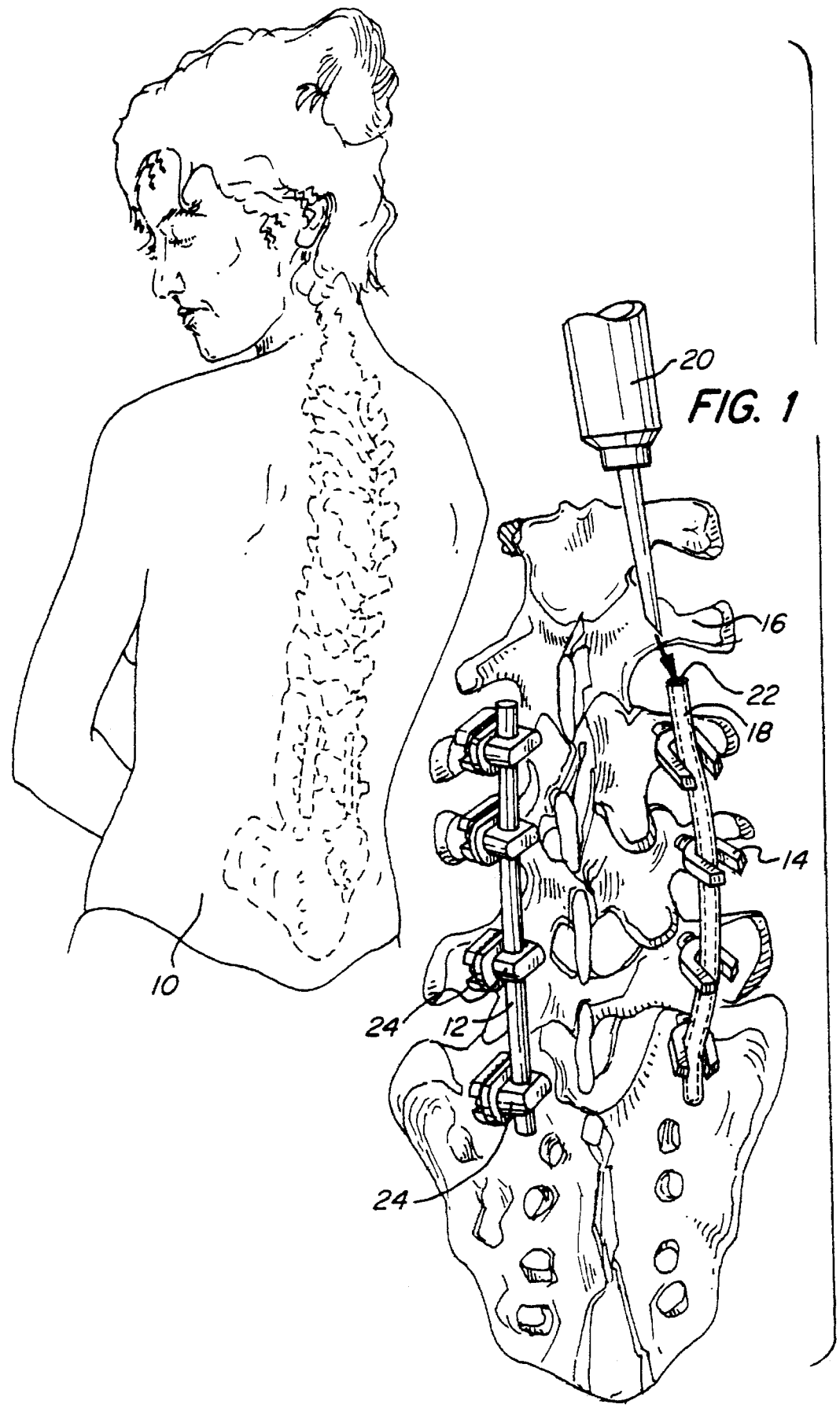
FIG. 1 is a schematic illustration of a section of a spinal column showing installation of a bilateral spinal bar support system according to the practice of the invention. During surgery, a quick-setting molding material is injected into flexible tubing placed in screw heads (shown to the right of the spine). After curing, the tubing is employed as a template for the fabrication of a precisely configured metal bar (shown installed to the left of the spine).

This invention is based upon the use of a quick-setting molding material to fabricate during surgery a bone fixation element such as a metal spinal support bar having the precise configuration required for the element. The quick-setting material is injected into a flexible tubing seated in the position where the element is required. The material is allowed to cure and harden for several minutes. After curing, the tubing is employed as a template for fabrication of an element, including one having complex compound curves.

In the practice of the method, an implantable rigid bone fixation element is shaped by inserting into at least two bone parts during surgery at least one securing means for the element, wherein each means is engageable with the bone and the element and defines a shape for the element after installation in the bone. Engagement means include, but are not limited to, screws, screw clamps, hooks, pins, clips, and the like. These have members such as clamps, heads or hooks that engage and secure the element. The securing means are installed in the medically dictated positions in the bone parts, and in the appropriate location and orientation to secure the implantable bone fixation element required. For spinal correction bars, this usually involves location of the clamp or screw members in the spine between adjacent spinal components, or in the sacrem, or both, as may be required for the medical problem being addressed.

The bone or bones to be fixed are typically aligned in the desired configuration after positioning of the securing means are inserted, but the bone or bones may be aligned before insertion in some embodiments. In other embodiments, the bone or bones may be partially aligned prior to insertion, e.g., when surgery is performed with a patient in traction, and then fully aligned to the desired configuration after insertion of the securing means. It is preferred that all of the securing means be set and the desired reconstruction, if performed, be completed before beginning the preparation of templates more fully described below.

Thereafter, with the affected portion of the bone or bones, e.g., vertebrae, in the appropriate location determined by the surgeon, a flexible housing having a an exterior contour essentially the same as the element is seated in the engaging means, such that the housing defines the shape of the element to be fabricated. Any flexible housing can be employed; preferred housings are tubings. The cross-section of the tubing can be circular, oval, square, rectangular, or other geometric shape desired for the element; cylindrical tubings are preferred in many embodiments. Typical tubings are flexible plastic such as silicone, Tygon® or Teflon®;

silicone tubings are preferred in some embodiments because of their flexibility, biocompatibility, and autoclavability. Clear or translucent tubings are preferred so that the injected material can be visually inspected. Typical tubings have a wall thickness of between about 0.5 and 3.2 mm. Example tubings useful for the fabrication of spinal rods or bars include, but are not limited to, 0.8 mm silicone tubing.

After the housing is seated in the channel, a fluid molding material is injected into the housing, typically using a syringe or applicator, and the material is cured for a time under conditions sufficient to harden the material so that the housing forms a temporary master having a shape which closely replicates the shape of the element. Any molding material may be employed; preferred molding materials are quick-setting and cure at room temperature after mixture of components in less than about 15 minutes at room temperature without shrinkage, but the time can be varied as required. Especially preferred for some embodiments are materials that cure in from about 2.5 to about 10 minutes. Example molding materials include, but are not limited to hydrophilic vinyl polysiloxane marketed under the names the Reprosil® cartridge system, caulk, or Dentsply®. Use of low, medium or high viscosity materials can be selected for making certain types of templates, and any combination of these materials can also be employed.

An embodiment of the invention is illustrated in the figures, which show schematically how spinal rods can be fabricated to fit the precise contours required for individual patients. FIG. 1 shows a method for shaping an implantable bilateral rigid spinal column support system for patient 10. In order to shape metal spinal bar 12, pedicle screws 14 are first inserted into vertebrae 16 in the appropriate configuration determined by the surgeon for affixing the support. Flexible tubing 18 is then seated in screws 14, and quick-setting molding material is injected from container 20 into tubing end 22 as indicated by the arrow. After the molding material cures, which as denoted above takes only a matter of minutes in preferred embodiments, the tubing containing the cured material defines the shape of the element to be fabricated and can be used as a template to form an element corresponding to bar 12, which is fastened to pedicle screws 14 by nuts 24.

Figure 2A:
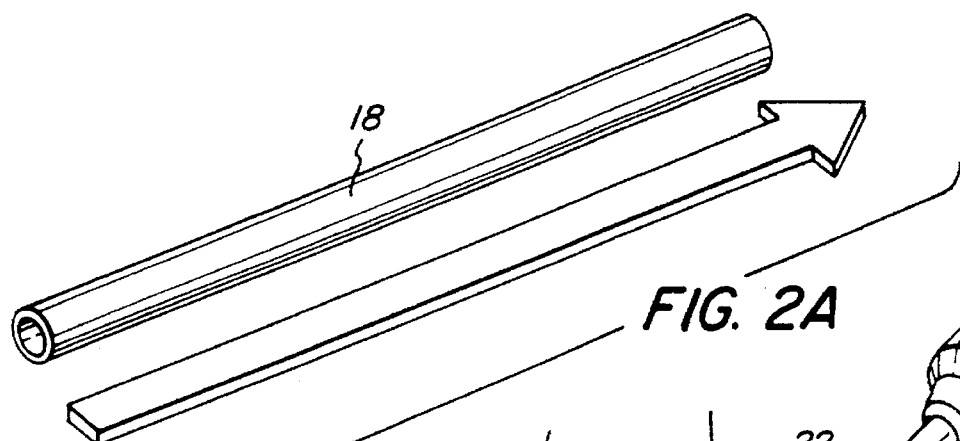
FIGS. 2A, 2B, and 2C further illustrate schematically some important features of the invention. The flexible tubing shown in FIG. 2A is placed in screw heads shown in FIG. 2B before injecting molding material into the tubing.
Figure 2B:
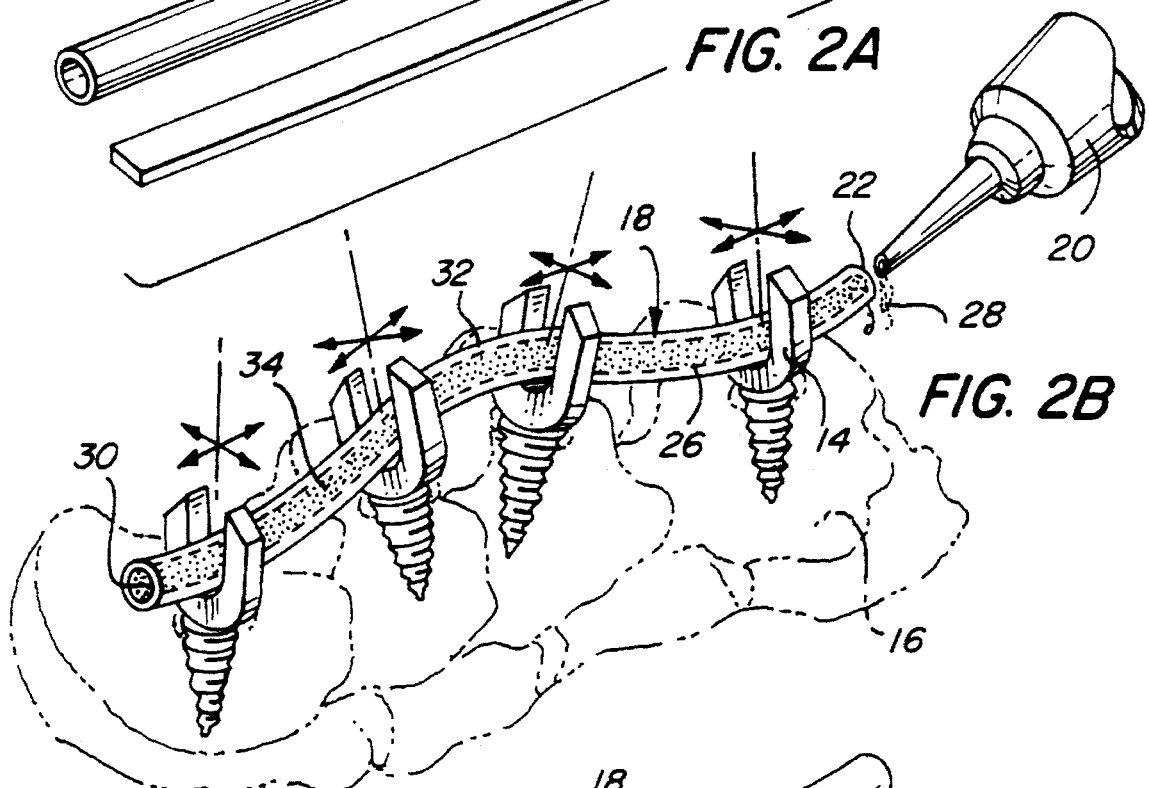
Figure 2C:
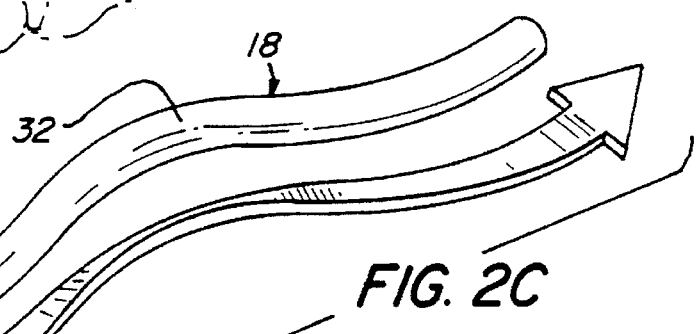

FIG. 2 further illustrates particulars about filling tubing with quick-setting molding material in the practice of this embodiment of the invention. FIG. 2A illustrates flexible tubing 18 prior to its use during the surgical procedure. As summarized above, screws 14 are positioned in vertebrae 16 to hold the bar to be fabricated. Tubing 18 is then seated in the screws as shown in FIG. 2B. So installed, it follows the contours of the bar to be fabricated, including, for example, curve 32 between the center screws 14. Fluid molding material 28 is injected into orifice 22 of tubing 18, where it cures inside tubing wall 34 to form hardened material 30. Tubing 18 containing cured and hardened molding material 30 can be lifted out of the screws as illustrated in FIG. 2C.

Figure 3:
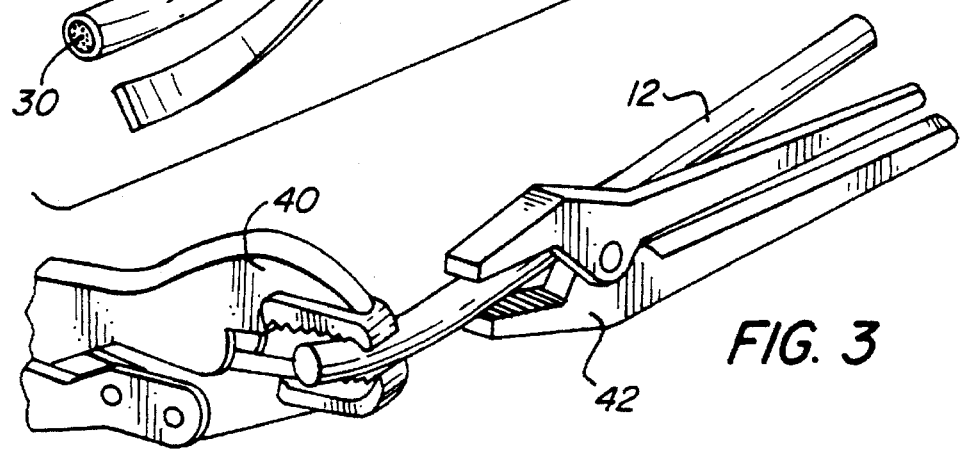
FIG. 3 shows a manual method of fashioning a metal bar using the hardened tubing template of FIG. 2C.

After the molding material has hardened as shown, the housing containing the cured material forms a rigid temporary master (FIG. 2C) that is used as a template to form the element. In preferred embodiments, the elements such as metal spinal support bars are shaped from the templates formed in situ in the operating room using manual, automatic or computer-assisted fabrication methods. Manual fabrication can be using any tools commonly employed to bend metal, such as, but not limited to, pliers, vises and the like. In FIG. 3, for example, support bar 12 is bent by opposing forces exerted by pliers 40 on vise 42 to produce a curve such as curve 32 in template 18 of FIG. 2C.

Figure 4:
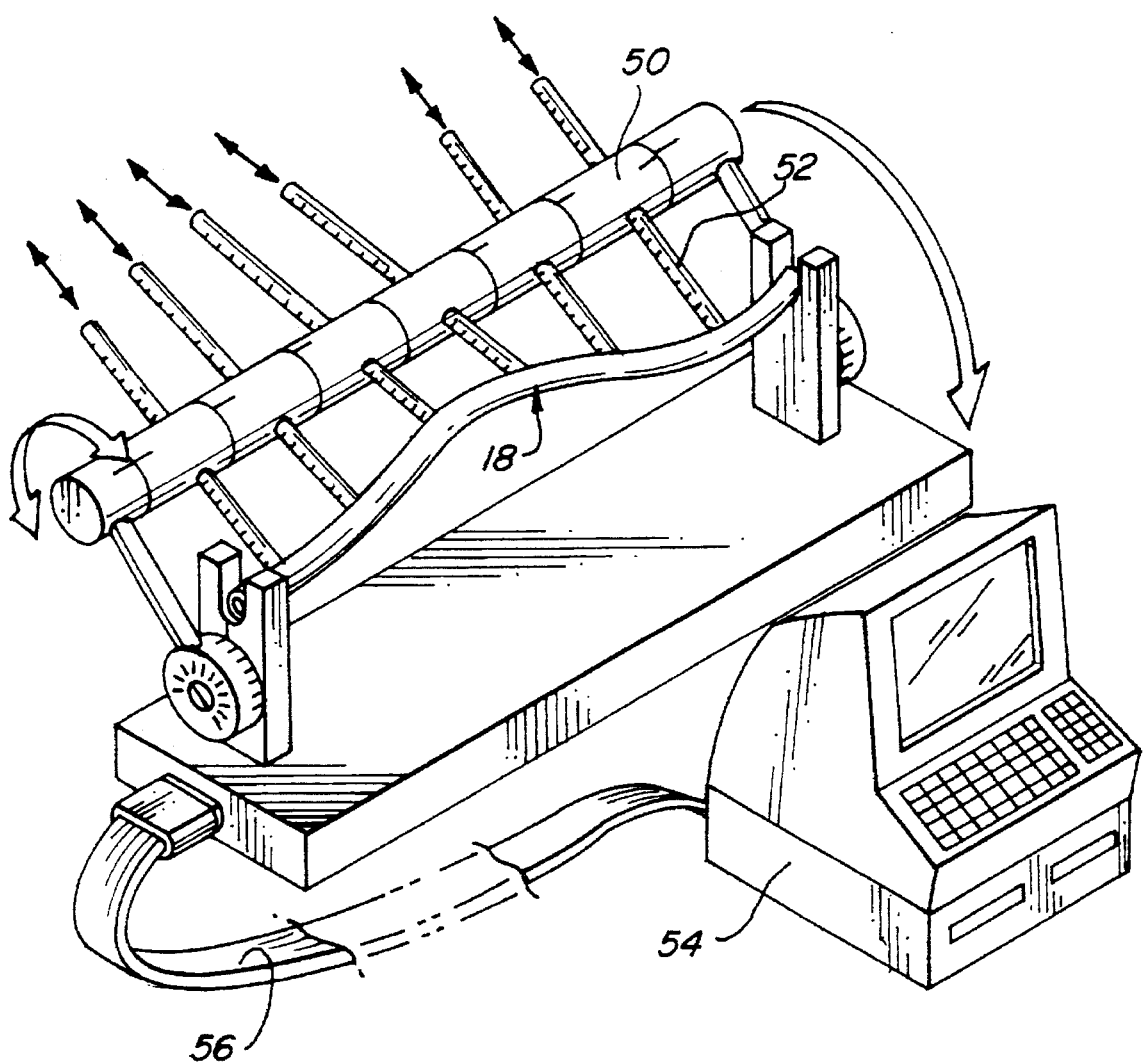
FIG. 4 illustrates computer fabrication of a bar using the same template. Both methods follow the precise contours of the template for fashioning the element.

Computer-assisted fabrication methods are preferred for complex elements. As illustrated in FIG. 4, this typically involves use of tubing 18 containing cured and hardened molding material 30 of FIG. 2C as a template in a device that measures curvature three-dimensionally using sensing means 52 fed into computer 54 by leads 56 as the device turns the temporary master in directions indicated by the arrows. Computer 54 is programmed to exactly duplicate the contours of tubing 18 containing hardened molding material 30 in a metal rod inside tube 50.

Thus in a preferred embodiment, the invention provides a method for shaping an implantable rigid spinal column support bar, including bars having at least one compound curve. As used herein, the term "bar" includes a single bar system and a system comprising a plurality of rods or bars forming segments aligned as a single bar for maintaining selected predetermined adjacent vertebrae in a predetermined orientation to inhibit front-to-back, side-to-side, and/or rotational movements of the supported portion of the spinal column. Though not specifically mentioned, it is understood that the procedure is carried out in the aseptic conditions of the operation suite and all instrumentation and components are in a sterile condition.

As illustrated above, the method involves first inserting securing means such as screw clamps or screws in the vertebrae in the portion of the spinal column to be supported by the bar; the securing means have members such as screw clamp members or screw heads that engage and secure the bar. Pedicle screws having a length of from about 25 to 55 mm and a diameter up to about 5 to 7 mm are employed in some embodiments; the screw heads are proportioned to attach to the bar, and have lateral or end slots or apertures for insertion of the bar.

After aligning the vertebrae in the spinal column in the desired position, a flexible hollow tubing is seated in the installed screw clamp members or heads to simulate the final position of the bar, wherein the tubing has an exterior diameter essentially the same as the bar. Typical tubings are cylindrical and have an exterior diameter of about 2 to about 7 mm, more narrowly from about 5 to about 6 mm. Since the tubing is soft and easily manually formed, it can be manipulated into position and inserted in the engaging means provided by the screw clamp members or heads to form a replication or master that follows the relative position of the screw heads and the delineates the shape of the bar to be fabricated. In preferred embodiments, two bars are shaped for bilateral support of the spinal column. In other embodiments, both a double and a single rod system may be employed, depending upon the particular case, e.g., where high localized rigidity is required.

A quick-setting fluid molding material such as Reprosil® or Dentsply® is then injected into the tubing, and the tubing and molding material are cured by waiting for 2.5 to 6 minutes until the material sets and hardens, so that the tubing forms a temporary master which follows and replicates the contour of the screw heads and can be used as a template to form a rigid rod sized to fit the determined contour. Once the bar is fashioned to the contour of the screw heads, the bar or pair of bars are installed in the proper position in the screw heads and checked for proper fit. After installation, the procedure is completed with a post-operative protocol set by the attending surgeon.

An advantage of the invention is that fabrication using the method of the invention gives a precisely contoured element, which minimizes the mechanical stresses, especially torquing, and screw fatigue, breakage, and pullout encountered in the use of rods shaped using other fabrication methods. Removal of shape uncertainty in fabrication also means that the success of the operation is somewhat less dependent upon surgical skill. Thus, the invention provides a safer, more reliable method of fabricating elements and reduces patient risk and complications.

Another advantage of the invention is that the fabrication procedure is shorter than previously employed trial-and-error template formations, so that surgery is shorter. The inventive method is used in the operating room under sterile conditions. The stress of more prolonged surgery on the patient is thus decreased.

The above description is for the purpose of illustrating and not limiting the present invention, and teaching the person of ordinary skill in the art how to practice the invention. It is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The references cited above are hereby incorporated by reference in in their entireties.

I claim:

1. A method for shaping an implantable rigid bone fixation element comprising:
   (a) inserting into at least two bone parts at least one securing means for the element, each means engageable with the bone and the element and defining a shape for the element after installation in the bone;
   (b) aligning the bone to be fixed in the desired configuration;
   (c) seating a flexible housing having an exterior contour essentially the same as the element engaging in the securing means;
   (d) injecting fluid molding material into the housing;
   (e) curing the molding material for a time under conditions sufficient to harden the material so that the housing forms a rigid temporary master having a shape which replicates the shape of the element; and
   (f) removing the temporary master and using it as a template to form the element.

2. A method according to claim 1 wherein the element is a spinal support bar, the bones are vertebrae, and the housing is flexible tubing having a diameter essentially the same as the bar.

3. A method according to claim 2 wherein the flexible tubing is clear or translucent silicone tubing.

4. A method according to claim 2 wherein the fluid molding material comprises a hydrophilic vinyl polysiloxane.

5. A method according to claim 4 wherein the material cures from about 2.5 to about 10 minutes at room temperature.

6. A method according to claim 2 wherein the securing means is a screw or screw clamp.

7. A method for shaping an implantable rigid spinal column support bar comprising:
   (a) inserting screws or screw clamps in the vertebrae in the portion of the spinal column to be supported by the bar, wherein the screws or screw clamps have screw members that engage and secure the bar,
   (b) aligning the column in the desired position;
   (c) seating flexible hollow tubing in the screw members to simulate the final position of the bar, said tubing having a diameter essentially the same as the bar,
   (d) injecting a quick-setting fluid molding material into the tubing,
   (d) curing the molding material for a time under conditions sufficient to harden the molding material in the tubing, and
   (e) removing the tubing containing the cured molding material and using it as a template for the formation of the bar.

8. A method according to claim 7 wherein the quick-setting fluid molding material comprises a hydrophilic vinyl polysiloxane.

9. A method according to claim 7 wherein the tubing is silicone.

10. A method according to claim 7 wherein two bars are shaped for bilateral support of the spinal column.

11. A method for shaping an implantable rigid spinal column support bar for maintaining selected predetermined adjacent vertebrae in a predetermined orientation to inhibit front-to-back, side-to-side, and rotational movements of the supported portion of the spinal column comprising:
   (a) inserting a plurality of pedicle screws in the vertebrae in the portion of the spinal column to be supported by the bar, wherein the screws have screw heads that are proportioned to engage and secure the bar;
   (b) aligning the vertebrae in the desired configuration to be supported;
   (c) seating flexible hollow tubing in the screw heads to simulate the final position and shape of the bar, said tubing having a diameter essentially the same as the bar;
   (d) injecting a quick-setting fluid molding material into the tubing;
   (e) curing the tubing and molding material for a time under conditions sufficient to harden the material in the tubing, so that the tubing forms a temporary master which follows the position of the screw heads and replicates the bar, and can be used as a template to form a rigid rod sized to fit the determined shape; and
   (e) removing the temporary master and using it as a template for the formation of the rod.

12. A method according to claim 11 wherein the tubing is silicone.

13. A method according to claim 11 wherein the fluid molding material comprises a hydrophilic vinyl polysiloxane and the filled tubing is cured from about 2.5 to about 10 minutes at room temperature to effect hardening.

14. A method according to claim 11 wherein at least two screws are inserted per vertebra and two bars are shaped for bilateral support of the spinal column.

15. A method according to claim 11 wherein the rod is shaped from the template using computer-assisted fabrication.

* * * * *